United States Patent [19]
Horn et al.

[11] Patent Number: 5,939,575
[45] Date of Patent: Aug. 17, 1999

[54] PROCESS FOR THE CONTINUOUS PREPARATION OF ACYLOXYSILANES

[75] Inventors: Michael Horn; Hartwig Rauleder; Claus-Dietrich Seiler; Jaroslaw Monkiewicz, all of Rheinfelden, Germany

[73] Assignee: Huels Aktiengesellshaft, Marl, Germany

[21] Appl. No.: 08/978,189

[22] Filed: Nov. 25, 1997

[30] Foreign Application Priority Data

Nov. 27, 1996 [DE] Germany .......................... 196 49 028

[51] Int. Cl.$^6$ ....................................................... C07F 7/08
[52] U.S. Cl. ................................................................ 556/442
[58] Field of Search .............................................. 556/442

[56] References Cited

U.S. PATENT DOCUMENTS

| | | |
|---|---|---|
| 5,187,291 | 2/1993 | Seiler et al. ............................ 556/442 |
| 5,387,706 | 2/1995 | Rasmussen et al. ..................... 556/442 |
| 5,523,446 | 6/1996 | Tolentino et al. ....................... 556/442 |
| 5,536,860 | 7/1996 | Monkiewicz et al. . |
| 5,646,325 | 7/1997 | Monkiewicz et al. . |

*Primary Examiner*—Paul F. Shaver
*Attorney, Agent, or Firm*—Oblon, Spivak, McClelland, Maier & Neustadt, P.C.

[57] ABSTRACT

Acyloxysilanes are prepared by a process of reacting an organochlorosilane with an excess of monocarboxylic anhydride at elevated temperature, thereby forming product acyloxysilane and by-product acyl chloride transferring the reaction mixture to the middle inlet of a separation tower having a still pot at its base, removing excess carboxylic anhydride by distillation at the tower top under reduced pressure, removing acyl chloride by-product from the separation tower, uniformly removing acyloxysilane from the tower still pot, and reacting virtually quantitatively the residual acid chloride present in the acyloxysilane removed from the still pot by adding a metal carboxylate to the acyloxysilane and separating the metal chlorides formed from the product.

17 Claims, 2 Drawing Sheets

5,939,575

PROCESS FOR THE CONTINUOUS PREPARATION OF ACYLOXYSILANES

BACKGROUND OF THE INVENTION

1. Field of the Invention

The present invention relates to a process for the continuous preparation of acyloxysilanes by reacting organochlorosilanes with essentially an excess of monocarboxylic anhydride at elevated temperature, separating the acyl chloride formed as by-product in the reaction and working up the remaining reaction mixture.

2. Description of the Background

Acyloxysilanes have many applications in the chemical industry. They are suitable, for example, as cross-linking silicon compounds in the preparation of compositions which are storable in the absence of water and hardenable at room temperature on exposure to moisture. Examples of such acyloxysilanes include methyl-, ethyl- and propyltris (ethanoyloxy) silane.

For silanes of this type, recently, there have been extreme increases in the requirements relating to their use with regard to purity, in particular with respect to the residual content of chlorine in the form of acid chloride. Residual chlorine contents in acyloxysilanes occur because of the incomplete reaction of all of the chlorine constituents of the organochlorosilane starting materials with the reagents which introduce the acyloxy group into the reaction. In the present invention, acid chloride is taken to mean chlorine which is bound to the silicon atom in a silane, hydrogen chloride, and chlorine present in an acyl chloride.

To prepare acyloxysilanes on an industrial scale, essentially two procedures are employed.

One procedure makes use of the reaction of organochlorosilanes with carboxylic acids to give the corresponding organoacyloxysilanes. This procedure is performed both batchwise and continuously. Batchwise preparation requires the presence of an inert solvent and long reaction times, in order to lower the residual acid chloride contents to values below 100 ppm (U.S. Pat. Nos. 2,437,073, 2,866,800, 3,974, 198, GB814 011). Continuous reactions of organochlorosilanes with carboxylic acids are disclosed in the publications DE 2 801 780, DE 3 221 702, EP 0 003 317, U.S. Pat. Nos. 4,332,956, 4,329,484. When use is made of small excesses of carboxylic acid, based on the amounts of organochlorosilane used, acid chloride contents remain of the orders of magnitude of up to 50 ppm by weight. Only the application of great excesses of carboxylic acid of the order of magnitude of 50% enables the acid chloride contents to be decreased to values below 1 ppm by weight, with unsatisfactory siloxane contents being tolerated.

The other procedure for preparing acyloxysilanes on an industrial scale makes use of the reaction of organochlorosilane with carboxylic anhydrides to give the corresponding organoacyloxysilanes.

FR 1 003 073 describes the batchwise and simultaneous preparation of acyloxysilanes and acyl chlorides by reading organochlorosilanes with monocarboxylic anhydrides. However, unsatisfactory product yields are obtained with undetectable residual chlorine contents being obtained after a reaction time of 8 hours.

A continuous method of preparing acyloxysilanes is disclosed in EP 0 509 213, in which organochlorosilanes are reacted with carboxylic anhydrides in the presence of special catalysts to give acyloxysilanes and acyl chlorides. The special procedure enables the acid chloride content to be decreased in the end products from, for example, 800 ppm by weight to 3 ppm by weight. However, lowering the acid chloride contents below the limits of detection can only be achieved with this procedure at the cost of greatly increased reaction times with the use of increased amounts of carboxylic anhydride.

The literature also describes procedures for preparing acyloxysilanes by reacting corresponding organochlorosilanes with alkali metal carboxylates in the presence of large amounts of inert diluents. These procedures are associated with the production of considerable amounts of salt and the need to remove the target product from the reaction mixture by complex washing processes. These procedures are scarcely practical on an industrial scale and also do not comply with current economic and ecological requirements (U.S. Pat. No. 2,573,302, GB 640 834, DE 870 554, U.S. Pat. Nos. 2,537,073, 2,866,800).

SUMMARY OF THE INVENTION

Accordingly, one object of the present invention is to provide a continuous economic process for preparing acyloxysilanes using a carboxylic anhydride as the acyloxylating reagent which enables preparation of a product having a residual acid chloride content of less than 2 ppm by weight of chlorine.

Another object of the present invention is to prevent the production of considerable amounts of solvent and to keep the production of salts as low as possible.

Briefly, these objects and other objects of the present invention as hereinafter will become more readily apparent can be attained in a process for the continuous preparation of acyloxysilanes by reacting an organochlorosilane with an excess of monocarboxylic anhydride at elevated temperature, thereby forming product acyloxysilane and by-product acyl chloride; transferring the reaction mixture to the middle inlet of a separation tower having a still pot at its base; removing excess carboxylic anhydride by distillation at the tower top under reduced pressure; removing acyl chloride by-product from the separation tower; uniformly removing acyloxysilane from the tower still pot; and reacting virtually quantitatively the residual acid chloride present in the acyloxysilane removed from the still pot by adding a metal carboxylate to the acyloxysilane and separating the metal chlorides formed from the product.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
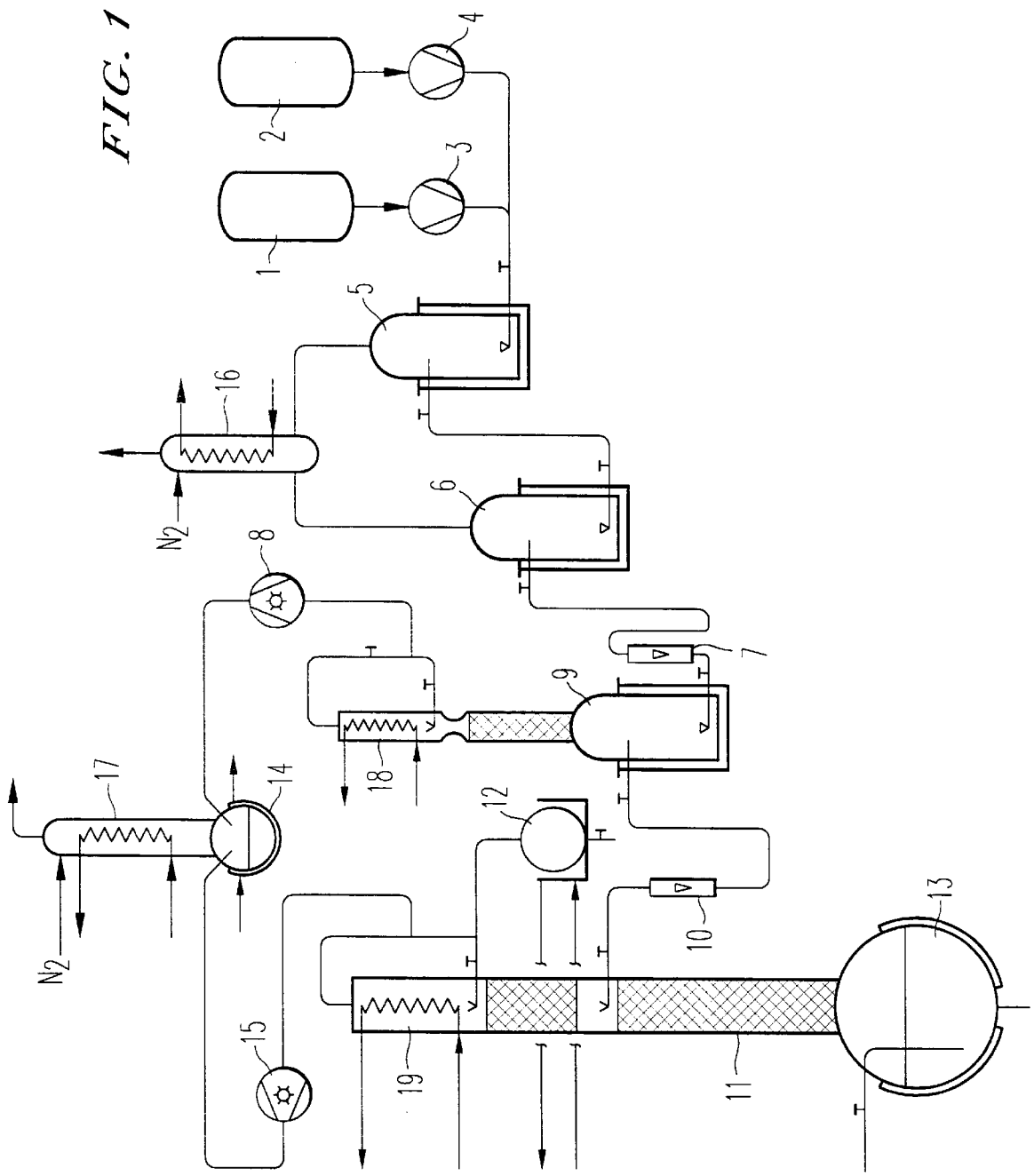
FIG. 1 is a diagram of a plant for preparing acyloxysilanes.

Surprisingly, it has now been found that it is possible, in a simple and economical manner, to decrease residual acid chloride contents in acyloxysilanes, as obtained, in particular in the process described in EP 0 509 213, to values considerably below 1 ppm by weight by adding a metal carboxylate to the prepared acyloxysilane and separating the metal chlorides formed. Significant amounts of solvent are not necessary in this procedure, and, furthermore, additional quantities of siloxanes are not formed in the product. Also, the amount of salts produced by this method is comparatively small.

Acyloxysilanes which can be prepared by the process of the invention have the formula:

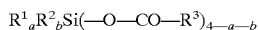

where a can have the value 3, 2 or 1 and b can have the value 1 or 0 and a+b≦3, preferably a=1 and b=0.

Suitable $R^1$ and $R^2$ groups represent hydrogen or saturated or unsaturated hydrocarbon radicals each having 1–10 carbon atoms, which may contain functional groups, e.g. halogen, which are not attacked under the specified reaction conditions, and also represent cyclic saturated or unsaturated hydrocarbon radicals having 6 carbon atoms. $R^1$ and $R^2$ can be identical or different in the present formula. $R^3$ represents, in particular, hydrogen, methyl, ethyl or propyl.

The compounds below are preferably prepared by the process of the invention:
 vinyltris(ethanoyloxy)silane
 ethyltris(ethanoyloxy)silane
 methyltris(ethanoyloxy)silane
 propyltris(ethanoyloxy)silane
 2-chloroethylmethylbis(ethanoyloxy)silane
 ethyltris(propanoyloxy)silane
 phenyltris(ethanoyloxy)silane.

Generally, the present process can be implemented in such a manner that an organochlorosilane is passed through one or more reactors at a temperature in the range from 25–100° C. together with essentially an excess of monocarboxylic anhydride and the addition of organic bases, their salts or organic acid amides which are soluble in the present mixture. The acyl chloride which forms in the reaction is removed, for example under reduced pressure, in a distillation reactor. Basic organic components which can be added here include, for example, tertiary, secondary or primary amines such as triethylamine or unsubstituted and/or N-substituted acid amides such as N,N-dimethylformamide. The reaction mixture remaining after separating the acyl chloride formed is worked-up to isolate the acyloxysilane. In a suitable manner, the work-up is performed such that the reaction mixture is transferred into the middle inlet of a tower, excess carboxylic anhydride is removed by distillation under reduced pressure at the top of the tower and acyloxysilane is removed at the tower still pot. Acyloxysilane removed in this manner generally has an acidic or hydrolyzable chlorine content of 2 ppm by weight or more. Generally, the residual acid chloride present in the acyloxysilane removed is then virtually quantitatively reacted with metal carboxylate added to the acyloxysilane and the metal chloride formed is separated from the acyloxysilane.

The metal carboxylate reactant, which removes residual acid chloride from the withdrawn or isolated acyloxysilane includes all known metal carboxylates of the elements of the Periodic Table which, in a suitable manner, form metal chloride salts. Preferred examples of metal carboxylates include sodium formate, sodium acetate, sodium propionate, sodium butyrate, potassium acetate, magnesium acetate, calcium acetate, barium acetate, zinc acetate and the like. Particularly preferred metal carboxylates include the carboxylates of the alkali metal elements and/or of the alkaline earth metal elements. Sodium carboxylates are particularly preferred. In a preferred manner, the metal carboxylates are used in the form of being dissolved in the carboxylic acid corresponding to the carboxylate employed. Usually, the residual acid chloride in the acyloxysilane is reacted with at least one metal carboxylate continuously at a temperature in the range from 0–200° C., preferably at 0–130° C., particularly preferably at 20–80° C. Depending on the properties of the substrate to be treated, the reaction temperature should if possible be selected so that the reaction time and the solubility of the resulting metal salts in the substrate are minimized. The reaction can be carried out both at reduced pressure, for example above 400 mbar absolute, and at atmospheric pressure or else elevated pressure, for example up to 2 bar absolute. In addition, it can be advantageous to react the organoacyloxysilanes with the metal carboxylates with stirring.

Preferably, the carboxylates are used here in amounts such that there is no excess over the stoichiometrically required amount, based on the acid chloride content in the substrate to be treated. Complete removal of the acid chloride in organoacyloxysilanes can be achieved either by a single addition of an appropriate amount of a metal carboxylate, or else in such a manner that, suitably, only approximately 70–80% of the amount of carboxylate stoichiometrically required for complete removal of the acid chloride in the substrate is metered in, the mixture is allowed to react, the residual acid chloride content is again determined and, depending on the level of the acid chloride content remaining in the substrate, 70–80% of the amount of carboxylate stoichiometrically required is metered in, i.e. a continuous product work-up, incorporating a quasi-continuous titration.

The metal chlorides formed in the reaction can likewise be separated off continuously in various ways, for example by filtration or centrifuging or decanting. Preferably, the metal salts are removed by centrifuging, using a continuous separator.

In addition, amounts of carboxylic acid which may still be present in the product can be removed by distillation during the work-up of the organoacyloxysilanes in the context of the continuous process of the invention.

The method of distillation can also be employed to separate product and metal salt. This method is used, in particular, if products having a particularly low siloxane content are to be obtained in the process of the invention.

In the present invention, the organoacyloxysilanes freed from residual chlorine shall be taken to mean those products whose acid chloride content is generally less than 2 ppm by weight, in particular less than 1 ppm by weight, preferably less than 0.5 ppm by weight of acid chloride, particularly preferably less than or equal to 0.1 ppm by weight.

The process according to the invention provides a process which enables acyloxysilanes containing significantly less than 1 ppm by weight of acid chloride to be continuously prepared in a good economical manner.

Having generally described this invention, a further understanding can be obtained by reference to certain specific examples which are provided herein for purposes of illustration only and are not intended to be limiting unless otherwise specified.

EXAMPLES

Comparison Example A

FIG. 1 shows the diagram of a plant for preparing acyloxysilanes. Ethyltrichlorosilane is charged into receiving vessel 1, and ethanoic anhydride into receiver 2. By means of metering pumps 3 and 4, 157 g (0.96 ml) of ethyltrichlorosilane per hour and 352 g (3.46 mol) of ethanoic anhydride per hour, admixed with 51 mg of triethylamine, are fed into the lower part of reactor 5 (volume=1 liter), in which the starting materials are heated to 60° C. After flowing through reactor 5, the reaction mixture passes via the cooler 16 into the reactor (volume=1 liter), in which it is kept at 60° C. and from which it is then charged via rotameter 7 into distillation reactor 9 (volume=1 liter) at a rate of approximately 510 g per hour. In this distillation reactor, the reaction mixture is heated to 90° C. and the previously formed and still forming ethanoyl chloride is removed by distillation from the reaction mixture at a pressure of 50–60 mbar (vacuum pump 8) and led off into cooled receiver 14 via condenser 18. The amount of ethanoyl chloride collected per hour in receiver 14 is approximately 216 g (2.76 mol).

Via rotameter 10, the product discharged from the upper part of distillation reactor 9 is passed into the middle inlet of the tower's distillation column 11, which consists of a 1.60 m long glass tube having a diameter of 5 cm and is filled with saddle bodies of 6 mm in diameter. Condenser 19 at the top of the tower and distillate receiver 12 receive a flow of coolant liquid (−27° C.). The lower end of the tower forms a 4-l jacketed flask 13, heated by a thermostat (circulation temperature approximately 125° C.). At a tower internal pressure of 5–7 mbar and a temperature of approximately 110° C. in tower still pot 13, the crude product fed in is worked-up. From jacketed flask 13, which is half-filled with liquid, ethyltris(ethanoyloxy)silane is continuously removed at a rate such that the liquid level in flask 13 remains unchanged. In the upper part of the tower, excess ethanoic anhydride is removed by distillation and is collected in the distillate receiver 12. At the top of the tower, via condenser 19 and vacuum pump 15, the residual ethanoyl chloride is distilled into receiver 14 which is provided with condenser 17.

The product removed from jacketed flask 13 consists of:

| | |
|---|---|
| ethyltris(ethanoyloxy)silane | 97.2% by weight |
| siloxanes | 1.7% by weight |
| ethanoic anhydride | 1.1% by weight |
| acid chloride | 3 ppm |

Comparison Example

The procedure described in Comparison Example A is repeated with the following alterations:

Instead of 157 g (0.96 mol) of ethyltrichlorosilane per hour and 352 g (3.46 mol) of ethanoic anhydride per hour, 235.5 g (144 mol) of ethyltrichlorosilane per hour and 528 g (5.19 mol) of ethanoic anhydride per hour, admixed with 76 mg of triethylamine, are fed into the reactor.

The product removed from jacketed flask 13, approximately 230 g per hour, consists of:

| | |
|---|---|
| ethyltris(ethanoyloxy)silane | approximately 97.7% by weight |
| siloxanes | approximately 1.2% by weight |
| ethanoic anhydride | approximately 1.1% by weight |
| acid chloride | approximately 35 ppm |

Example 1

Figure 2:
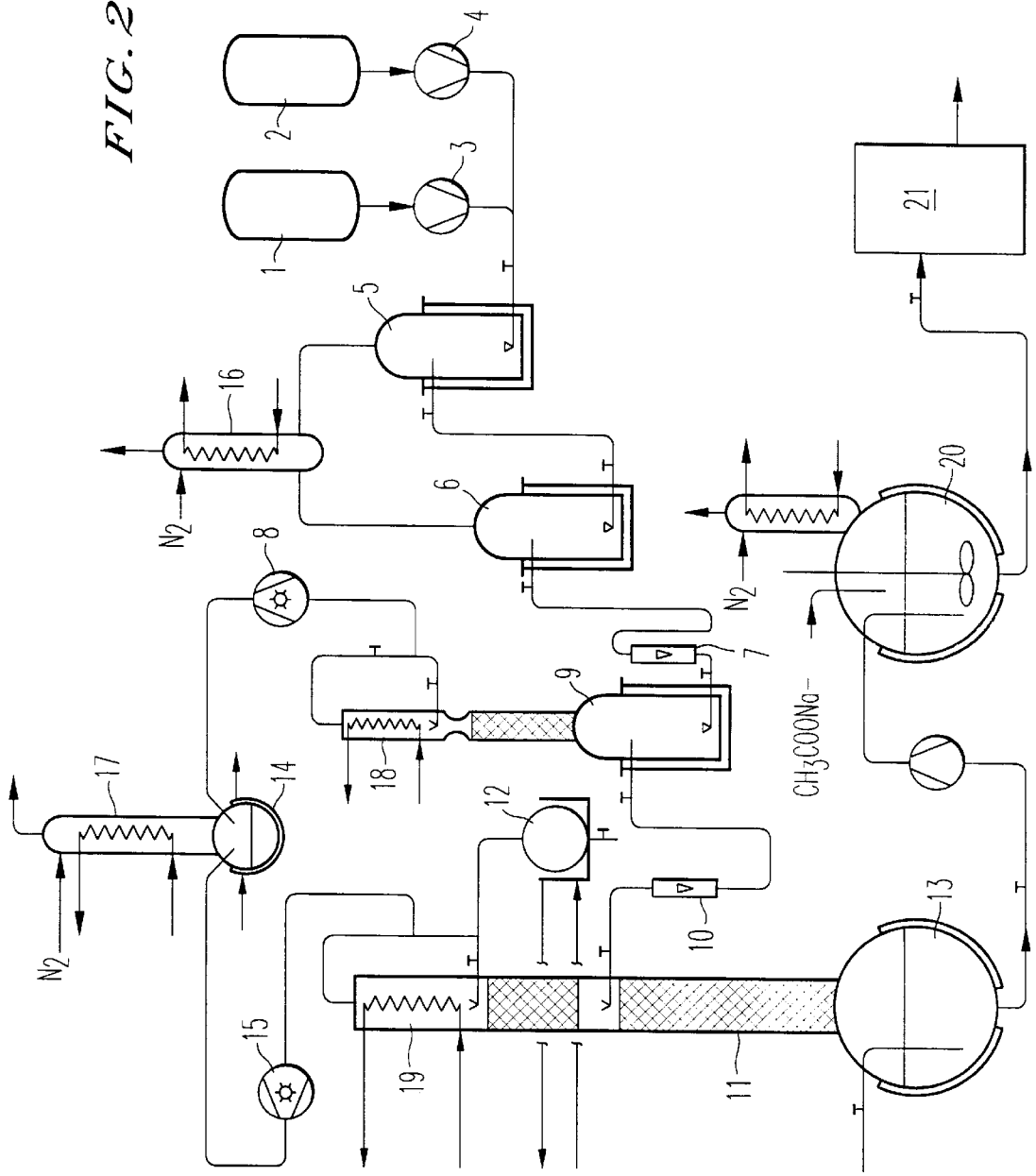
FIG. 2 is a diagram of the plant of FIG. 1 further comprising a receiver flask.

The procedure described in Comparison Example B is repeated with the following alterations:

The apparatus shown in FIG. 1 is supplemented by a receiver flask 20, which is equipped with an upstream feed device, jacket, agitator, attached condenser, thermometer and bottom outlet port, as shown in FIG. 2.

From the tower still pot 13, a product mixture of constant composition, whose acid chloride content is 41 ppm by weight, is removed and transferred to the receiver flask 20 which is heated by a heating circuit to 90° C. The amount of product uniformly removed from tower still pot 13 is approximately 230 g per hour.

In the course of one hour, an amount of 0.266 g of a solution of 8.0 g of sodium methoxide in 92.0 g of acetic acid is added to receiver flask 20. The suspension of sodium chloride and product which forms in the receiver flask is cooled and passed through a separator 21, and then, if appropriate, additionally through a fine filter. The product freed from sodium chloride consists of:

| | |
|---|---|
| ethyltris(ethanoyloxy)silane | 97.6% by weight |
| siloxanes | 1.1% by weight |
| ethanoic anhydride | 1.2% by weight |
| acetic acid | 0.1% by weight |
| acid chloride | approximately 0.1 ppm by weight |

The disclosure of German priority application 196 49 028.6 having a filing date of Nov. 27, 1996 is hereby incorporated by reference.

Obviously numerous modifications and variations of the present invention are possible in light of the above teachings. It is, therefore, to be understood that within the scope of the appended claims, the invention may be practiced otherwise than as specifically described herein.

What is claimed is as new and is desired to be secured by Letters Patent of the United States is:

1. A process for the continuous preparation of acyloxysilanes:

reacting an organochlorosilane with an excess of monocarboxylic anhydride at elevated temperature, thereby forming product acyloxysilane and by-product acyl chloride;

transferring the reaction mixture to the middle inlet of a separation tower having a still pot at its base;

removing excess carboxylic anhydride by distillation at the tower top under reduced pressure;

removing acyl chloride by-product from the separation tower;

uniformly removing acyloxysilane from the tower still pot; and reacting virtually quantitatively the residual acid chloride present in the acyloxysilane removed from the still pot by adding a metal carboxylate to the acyloxysilane and separating the metal chlorides formed from the product.

2. The process as claimed in claim 1, wherein the residual acid chloride present is reacted virtually quantitatively by adding at least one metal carboxylate, the carboxylate anion of which corresponds to the acyloxy component of the acyloxysilane.

3. The process as claimed in claim 1, wherein dissolved metal carboxylate is added to the acyloxysilane removed.

4. The process as claimed in claim 3, wherein the metal carboxylate is dissolved in the carboxylic acid corresponding to the carboxylate anion of the metal carboxylate.

5. The process as claimed in claim 1, wherein the metal carboxylate is a carboxylate of an alkali metal element and/or of an alkaline earth metal element.

6. The process as claimed in claim 1, which comprises adding the metal carboxylate or a solution thereof in an amount up to an equivalent amount with respect to the amount of acid chloride actually present in the acyloxysilane.

7. The process as claimed in claim 1, wherein the reaction of the acid chloride with metal carboxylate is carried out continuously at a temperature ranging from 0–130° C.

8. The process as claimed in claim 7, wherein the reaction of the acid chloride with metal carboxylate is carried out continuously at a temperature ranging from 20–80° C.

9. The process as claimed in claim 1, wherein the reaction of the acid chloride with metal carboxylate is carried out with stirring.

10. The process as claimed in claim 1, wherein the metal chloride formed in the reaction is separated by continuous filtration.

11. The process as claimed in claim 1, wherein the metal carboxylate is sodium formate, sodium acetate, sodium propionate, sodium butyrate, potassium acetate, magnesium acetate, calcium acetate, barium acetate or zinc acetate.

12. The process as claimed in claim 1, wherein the reaction medium contains an organic base or organic acid amide.

13. The process as claimed in claim 12, wherein said amide is N,N-dimethylformamide.

14. The process as claimed in claim 12, wherein said base is a primary, secondary or tertiary amine.

15. The process as claimed in claim 14, wherein said base is triethylamine.

16. The process as claimed in claim 1, wherein the reaction between metal carboxylate and residual acid chloride in the acyloxysilane occurs at a temperature of 0–200° C.

17. The process as claimed in claim 16, wherein said temperature ranges from 0–130° C.

* * * * *